United States Patent [19]

Mihm et al.

[11] Patent Number: 5,565,469

[45] Date of Patent: Oct. 15, 1996

[54] BENZIMIDAZOLES AND PHARMACEUTICAL COMPOSITIONS CONTAINING THEM

[75] Inventors: Gerhard Mihm, Biberach; Norbert Hauel, Schemmerhofen; Uwe Ries, Biberach; Jacobus C. Antonius van Meel, Mittelbiberich; Wolfgang Wienen, Biberach/Rissegg; Michael Entzeroth, Warthausen, all of Germany

[73] Assignee: Dr. Karl Thomae GmbH, Biberach an der Riss, Germany

[21] Appl. No.: 402,744

[22] Filed: Mar. 13, 1995

[30] Foreign Application Priority Data

Mar. 14, 1994 [DE] Germany .............................. 94408497

[51] Int. Cl.⁶ ...................... A61K 31/435; C07D 471/04
[52] U.S. Cl. ........................... 514/300; 546/121; 548/183; 548/214; 548/305.4
[58] Field of Search .................... 546/121; 514/300

[56] References Cited

U.S. PATENT DOCUMENTS 5,385,925  1/1995  Narr et al. ............................. 514/382

FOREIGN PATENT DOCUMENTS

| | | |
|---|---|---|
| 0392317 | 10/1990 | European Pat. Off. . |
| 0459136 | 12/1991 | European Pat. Off. . |
| 0468470 | 1/1992 | European Pat. Off. . |
| 0502314 | 9/1992 | European Pat. Off. . |
| 0520423 | 12/1992 | European Pat. Off. . |
| 0543263 | 5/1993 | European Pat. Off. . |
| 0556789 | 8/1993 | European Pat. Off. . |
| 0566020 | 10/1993 | European Pat. Off. . |
| 4212748 | 10/1993 | Germany . |

*Primary Examiner*—Bernard Dentz
*Attorney, Agent, or Firm*—Robert P. Raymond; Wendy E. Rieder; Alan R. Stempel

[57] ABSTRACT

Angiotensin-II inhibiting benzimidazoles, useful for the treatment of hypertension. Exemplary compounds are:

(a) 4'-[(2-n-propyl-4-methyl-6-(1-methylbenzimidazol-2-yl)-benzimidazol-1-yl)-methyl]-2-(1,3-thiazolidin-2,4-dione-5-methylidinyl)-biphenyl, (b) 4'-[(2-n-propyl-4-methyl-6-(1-methylbenzimidazol-2-yl)-benzimidazol-1-yl)-methyl]-2-sulpho-biphenyl, (c) 4'-[(2-ethyl-4-methyl-6-(5,6,7,8-tetrahydro-imidazo[1,2-a]pyridin-2-yl)-benzimidazol-1-yl)-methyl]-2-sulpho-biphenyl, (d) 4'-[(2-n-propyl-4-methyl-6-(1-methylbenzimidazol-2-yl)-benzimidazol-1-yl)-methyl]-2-trifluoroacetylamino-biphenyl, (e) 4'-[(2-ethyl-4-methyl-6-(5,6,7,8-tetrahydro-imidazo[1,2-a]pyridin-2-yl)-benzimidazol-1-yl)-methyl]-2-trifluoroacetylamino-biphenyl, (f) 4'-[(2-n-propyl-4-methyl-6-(1-methylbenzimidazol-2-yl)-benzimidazol-1-yl)-methyl]-2-(4-methoxy-benzylaminocarbonylaminosulphonyl)-biphenyl, (g) 4'-[(2-n-propyl-4-methyl-6-(1-methylbenzimidazol-2-yl)-benzimidazol-1-yl)-methyl]-2-(cyclohexylamino-carbonylaminosulphonyl)-biphenyl, (h) 4'-[(2-n-propyl-4-methyl-6-(1-methylbenzimidazol-2-yl)-benzimidazol-1-yl)-methyl]-2-(benzoylamino-sulphonyl)-biphenyl, (i) 4'-[(2-ethyl-4-methyl-6-(5,6,7,8-tetrahydro-imidazo[1,2-a]pyridin-2-yl)-benzimidazol-1-yl)-methyl]-2-(benzoylaminosulphfonyl)-biphenyl, (j) 4'-[(2-n-butyl-4-methyl-6-(propanesultam-1-yl)-benzimidazol-1-yl)-methyl]-2-(benzoylaminosulphonyl)-biphenyl and (k) 4'-[(2-ethyl-4-methyl-6-(5,6,7,8-tetrahydro-imidazo[1,2-a]pyridin-2-yl)-benzimidazol-1-yl)-methyl]-2-(cyclohexylaminocarbonylaminosulphonyl)-biphenyl.

8 Claims, No Drawings

BENZIMIDAZOLES AND PHARMACEUTICAL COMPOSITIONS CONTAINING THEM

The present invention relates to new benzimidazoles of the general formula

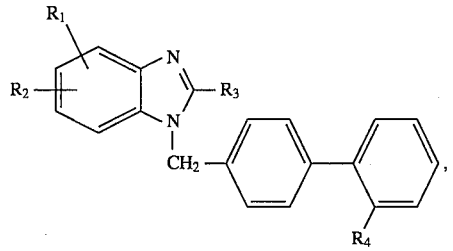

the tautomers and the salts thereof, particularly for pharmaceutical use the physiologically acceptable salts thereof, which have valuable pharmacological properties, as they are angiotensin-antagonists, particularly angiotensin-II-antagonists, pharmaceutical compositions containing these compounds, their use and processes for preparing them.

In general formula I above:

$R_1$ denotes a fluorine, chlorine or bromine atom, a $C_{1-3}$-alkyl group or a trifluoromethyl group;

$R_2$ denotes a 5-membered heteroaryl group bound via a carbon atom and containing an imino group, an oxygen or sulphur atom or an imino group and an oxygen, sulphur or nitrogen atom, and to which there may be attached, via two adjacent carbon atoms, an n-propylene, n-butylene or 1,3-butadienylene bridge or, via an imino group and an adjacent carbon atom, an n-butylene or 1,3-butadienylene bridge, whilst the carbon skeleton of the above-mentioned bicyclic rings may be mono- or disubstituted by a fluorine, chlorine or bromine atom, by a trifluoromethyl, alkyl, alkoxy, cyano, aminocarbonyl, carboxy, nitro, amino, alkylamino, dialkylamino or alkoxy group each having 1 to 3 carbon atoms in the alkyl or alkoxy moiety, whilst the substituents may be identical or different, and additionally an HN— group of the above-mentioned heteroaromatic rings may be substituted by a $C_{1-6}$-alkyl group, a phenylalkyl group having 1 to 3 carbon atoms in the alkyl moiety or a $C_{3-6}$-cycloalkyl group, or $R_2$ denotes an imidazol-4-yl group substituted by a $C_{1-3}$-alkyl group, wherein the alkyl moiety may be substituted in the 2- or 3-position by a dimethylamino, diethylamino, pyrrolidino, piperidino, hexamethyleneimino or morpholino group, a pyrrolidino, piperidino or hexamethyleneimino group in which a methylene group is replaced by a carbonyl or sulphonyl group, a maleic acid imido group optionally substituted by a $C_{1-3}$-alkyl group or by a phenyl group, or an imidazolidin-2,4-dion-3-yl group optionally substituted by a $C_{1-3}$-alkyl group;

$R_3$ denotes a $C_{1-4}$-alkyl group, a $C_{3-5}$-cycloalkyl group, an alkoxy or alkylthio group having 1 to 3 carbon atoms in the alkyl moiety; and $R_4$ denotes an amino group optionally substituted by an alkoxycarbonyl group having a total of 2 to 6 carbon atoms or by a trifluoroacetyl or trifluoromethylsulphonyl group, a sulphonyl group substituted by a hydroxy, amino, alkylcarbonylamino, alkoxycarbonylamino, alkylaminocarbonylamino, dialkylaminocarbonylamino, cycloalkylcarbonylamino, cycloalkylaminocarbonylamino, phenylcarbonylamino, phenylaminocarbonylamino, phenylalkylcarbonylamino or phenylalkylaminocarbonylamino group, wherein the alkyl moiety may contain 1 to 3 carbon atoms, the cycloalkyl moiety may contain 5 to 7 carbon atoms and the phenyl nucleus may be substituted by a fluorine, chlorine or bromine atom or by a methoxy group, or a hydroxycarbamidoyl, thiazolidin-2,4-dione-5-methylidene or 2,5-dihydro-5-oxo-oxadiazol-3-yl group.

Examplary definitions of the groups $R_1$ to $R_4$ are:

$R_1$ may represent a fluorine, chlorine or bromine atom, a methyl, ethyl, n-propyl, isopropyl or trifluoromethyl group, $R_2$ may represent a 1-methyl-imidazol-4-yl, 1-ethyl-imidazol-4-yl, 1-n-propylimidazol- 4-yl, 1-isopropyl-imidazol-4-yl, 1-(2-dimethylamino-ethyl)-imidazol-4-yl, 1-(3-dimethylamino-propyl)-imidazol-4-yl, 1-(2-diethylamino-ethyl)-imidazol-4-yl, 1-(3-diethylamino-propyl)-imidazol-4-yl, 1-(2-pyrrolidino-ethyl)-imidazol-4-yl, 1-(3 -pyrrolidino-propyl)-imidazol- 4-yl, 1-(2-piperidino-ethyl)-imidazol-4-yl, 1-(3-piperidino-propyl)-imidazol- 4-yl, 1-(2-hexamethyleneimino-ethyl)-imidazol-4-yl, 1-(3-hexamethyleneimino-propyl)-imidazol-4-yl, 1-(2-morpholino-ethyl)-imidazol-4-yl, 1-(3-morpholino-propyl)-imidazol-4-yl, 2-oxo-pyrrolidino, 2-oxo-piperidino, 2-oxo-hexamethyleneimino, propanesultam-1-yl, butanesultam-1-yl, pentanesultam-1-yl, maleic acid imido, 2-methyl-maleic acid imido, 2-phenyl-maleic acid imido, 4,5-trimethylene-imidazol- 2-yl, 4,5-trimethylene-1-methyl-imidazol-2-yl, 4,5-trimethylene-1-n-butyl-imidazol-2-yl, 4,5-trimethylene-1-n-hexyl-imidazol-2-yl, 4,5-trimethylene- 1-cyclopropyl-imidazol-2-yl, 4,5-trimethylene-1-cyclohexyl-imidazol-2-yl, benzimidazol-2-yl, 1-methylbenzimidazol-2-yl, 1-ethylbenzimidazol-2-yl, 1-n-propylbenzimidazol- 2-yl, 1-isopropylbenzimidazol-2-yl, 1-n-butylbenzimidazol-2-yl, 1-isobutylbenzimidazol-2-yl, 1-n-pentylbenzimidazol-2-yl, 1-n-hexylbenzimidazol-2-yl, 1-cyclopropylbenzimidazol-2-yl, 1-cyclobutylbenzimidazol-2-yl, 1-cyclopentylbenzimidazol- 2-yl, 1-cyclohexylbenzimidazol-2-yl, 5-nitrobenzimidazol-2-yl, 5-amino-benzimidazol-2-yl, 5-acetamidobenzimidazol-2-yl, 5-methylbenzimidazol- 2-yl, 5-methoxybenzimidazol-2-yl, 5-ethoxy-benzimidazol-2-yl, 1-methyl- 5-methoxybenzimidazol-2-yl, 1,5-dimethyl-benzimidazol-2-yl, 1,6-dimethylbenzimidazol- 2-yl, 1,4-dimethyl-benzimidazol-2-yl, 5,6-dimethyl-benzimidazol-2-yl, 1,5,6-trimethyl-benzimidazol-2-yl, 5-chloro-benzimidazol-2-yl, 5-chloro-1-methylbenzimidazol-2-yl, 6-chloro-1-methyl-benzimidazol-2-yl, 5,6-dichloro-1 -methyl-benzimidazol-2-yl, 5-dimethylamino-benzimidazol-2-yl, 5-dimethylamino-1-methyl-benzimidazol-2-yl, 5,6-dimethoxy- 1-methyl-benzimidazol-2-yl, 5,6-dimethoxy-1-ethyl-benzimidazol-2-yl, 5-fluoro-1-methyl-benzimidazol-2-yl, 6-fluoro-1-methyl-benzimidazol-2-yl, 5-trifluoromethyl-benzimidazol- 2-yl, 5-trifluoromethyl-1-methyl-benzimidazol-2-yl, 4-cyano-1-methyl-benzimidazol-2-yl, 5-carboxy-1-methyl-benzimidazol-2-yl, 5-aminocarbonyl-benzimidazol-2-yl, 5-aminocarbonyl-1-methyl-benzimidazol-2-yl, 4,5, 6,7-tetrahydro-benzimidazol-2-yl, 4,5,6,7-tetrahydro-1-methyl-benzimidazol-2-yl, 4,5,6,7-tetrahydro-1-ethyl-benzimidazol-2-yl, 4,5,6,7-tetrahydro-1-n-butylbenzimidazol- 2-yl, 4,5,6,7-tetrahydro-1-n-hexyl-benzimidazol-2-yl, 4,5,6,7-tetrahydro- 1-cyclopropyl-benzimidazol-2-yl, 4,5,6,7-tetrahydro-1-cyclohexylbenzimidazol- 2-yl, imidazo[1,2-a]pyridin- 2-yl, 5-methyl-imidazo[1,2-a]pyridin-2-yl, 6-methyl-imidazo[1,2-a]pyridin-2-yl, 7-methyl-imidazo[1,2-a]pyridin-2-yl, 8-methyl-imidazo[1,2-a]pyridin-2-yl, 5,7-dimethylimidazo[1,2-a]pyridin-2-yl, 5,6,7,8-tetrahydro-imidazo[1,2-a]pyridin-2-yl, imidazo[1,2-a]pyrimidin-2-yl, imidazo[4,5-b]pyridin-2-yl, 1-methyl-imidazo[4,5-b]pyridin-2-yl, 1-n-hexyl-imidazo[4,5-b]pyridin-2-yl, 1-cyclopropylimidazo[4,5-b]pyridin-2-yl, 1-cyclohexyl-imidazo[4,5-b]pyridin-2-yl, 6-methylimidazo[4,5-b]pyridin-2-yl, 1,6-dimethyl-imidazo[4,5-b]pyridin-2-yl, imidazo[4,5-c]pyridin-2-yl, 1-methyl-imidazo[4,5-c]pyridin-2-yl, 1-n-hexyl-imidazo[4,5-c]pyridin-2-yl, 1-cyclopropyl-imidazo[4,5-c]pyridin-2-yl, 1-cyclohexylimidazo[4,5-c]pyridin-2-yl, imidazo[2,1-b]thiazol-6-yl, imidazo[1,2-c]pyrimidin-2-yl, imidazo[1,2-a]pyrazin-2-yl, imidazo[1,2-b]pyridazin-2-yl, imidazo[4,5-c]pyridin-2-yl, purin-8-yl, imidazo[4,5-b]pyrazin-2-yl, imidazo[4,5-c]pyridazin-2-yl, imidazolidin-2,4-dion-3-yl or 5-methyl-imidazolidin-2,4-dion-3-yl group, $R_3$ may represent a methyl, ethyl, n-propyl, isopropyl, n-butyl, 1-methyl-n-propyl, 2-methyl-n-propyl, tert.butyl, cyclopropyl, cyclobutyl, cyclopentyl, methoxy, ethoxy, n-propoxy, isopropoxy, methylthio, ethylthio, n-propylthio or isopropylthio group and $R_4$ may represent a formyl, hydroxymethyl, amino, methoxycarbonylamino, ethoxycarbonylamino, propoxycarbonylamino, tert.butoxycarbonylamino, trifluoroacetylamino, trifluoromethylsulphonylamino, sulpho, sulphamoyl, methoxycarbonylaminosulphonyl, ethoxycarbonylaminosulphonyl, propoxycarbonylaminosulphonyl, tert.butoxycarbonylaminosulphonyl, acetylaminosulphonyl, propionylaminosulphonyl, butanoylaminosulphonyl, methylaminocarbonylaminosulphonyl, ethylaminocarbonylaminosulphonyl, n-propylaminocarbonylaminosulphonyl, isopropylaminocarbonylaminosulphonyl, methylaminocarbonylaminosulphonyl, N,N-dimethylaminocarbonylaminosulphonyl, N,N-diethylaminocarbonylaminosulphonyl, cyclohexylcarbonylaminosulphonyl, cycloheptylcarbonylaminosulphonyl, cyclopentylaminocarbonylaminosulphonyl, cyclohexylaminocarbonylaminosulphonyl, cycloheptylaminocarbonylaminosulphonyl, phenylcarbonylaminosulphonyl, 4-fluoro-phenylcarbonylaminosulphonyl, 4-chloro-phenylcarbonylaminosulphonyl, 4-bromo-phenylcarbonylaminosulphonyl, 4-methoxy-phenylcarbonylaminosulphonyl, phenylaminocarbonylaminosulphonyl, 4-fluoro-phenylaminocarbonylaminosulphonyl, 4-chloro-phenylaminocarbonylaminosulphonyl, 4-bromo-phenylaminocarbonylaminosulphonyl, 4-methoxy-phenylaminocarbonylaminosulphonyl, benzylaminocarbonylaminosulphonyl, 4-fluoro-benzylaminocarbonylaminosulphonyl, 4-chloro-benzylaminocarbonylaminosulphonyl, 4-bromo-benzylaminocarbonylaminosulphonyl, 4-methoxy-benzylaminocarbonylaminosulphonyl, 2-phenylethylaminocarbonylaminosulphonyl, 2-(4-fluoro-phenyl)ethylaminocarbonylaminosulphonyl, 2-(4-chlorophenyl)ethylaminocarbonylaminosulphonyl, 2-(4-bromo-phenyl)ethylaminocarbonylaminosulphonyl, 2-(4-methoxy-phenyl)-ethylaminocarbonylaminosulphonyl, 3-phenylpropylaminocarbonylaminosulphonyl, 3-(4-fluoro-phenyl)propylaminocarbonylaminosulphonyl, 3-(4-chloro-phenyl)propylaminocarbonylaminosulphonyl, 3-(4-bromo-phenyl)propylaminocarbonylaminosulphonyl, 3-(4-methoxy-phenyl)propylaminocarbonylaminosulphonyl, hydroxycarbamidoyl, 1,3-thiazolidin-2,4-dion-5-methylidene or 1,2,4-oxadiazol-5-on-3-yl group.

Preferred compounds of general formula I above are those wherein $R_1$ denotes a methyl group, $R_2$ denotes a benzimidazol-2-yl group optionally methyl-substituted in the 1-position, an imidazol-4-yl group optionally substituted in the 1-position by a $C_{1-3}$-alkyl group, wherein the alkyl substituent may be substituted in the 2- or 3-position by a morpholino group, or $R_2$ denotes a 5,6,7,8-tetrahydro-imidazo[1,2-a]pyridin-2-yl, propanesultam-1-yl or butanesultam-1-yl group, $R_3$ denotes a straight-chained $C_{2-4}$-alkyl group and $R_4$ denotes an amino group, a sulphonyl group substituted by a hydroxy, amino, dimethylaminocarbonylamino, phenylcarbonylamino, cycloalkylaminocarbonylamino or benzylaminocarbonylamino group, wherein the cycloalkyl moiety may contain 5 or 6 carbon atoms and the phenyl moiety may be substituted by a methoxy group, or $R_4$ may denote a trifluoroacetylamino, tert.butoxycarbonylamino, trifluoromethylsulphonylamino, 1,3-thiazolidin-2,4-dione-6-methylidene or 1,2,4-oxadiazol-5-on-3-yl group, the tautomers and the salts thereof.

Particularly preferred compounds of general formula I above are those wherein $R_1$ in the 4-position represents a methyl group, $R_2$ in the 6-position represents a benzimidazol-2-yl group optionally methyl-substituted in the 1-position, an imidazol-4-yl group optionally substituted in the 1position by a $C_{1-3}$-alkyl group (wherein the alkyl substituent may be substituted in the 2- or 3-position by a morpholino group), or a 5,6,7,8-tetrahydroimidazo[1,2-a]pyridin-2-yl, propanesultam-1-yl or butanesultam-1-yl group, $R_3$ denotes a straight-chained $C_{2-4}$-alkyl group and $R_4$ denotes a sulphonyl group substituted by a hydroxy, amino, dimethylaminocarbonylamino, phenylcarbonylamino, cycloalkylaminocarbonylamino or benzylaminocarbonyl-amino group, wherein the cycloalkyl moiety may contain 5 or 6 carbon atoms and the phenyl moiety may be substituted by a methoxy group, or $R_4$ denotes a trifluoroacetylamino, trifluoromethylsulphonylamino, 1,3-thiazolidin-2,4-dione-5-methylidene or 1,2,4-oxadiazol-5-on-3-yl group, and the salts thereof.

Most specially preferred compounds of the above general formula I are those wherein $R_1$ in the 4-position denotes a methyl group, $R_2$ in the 6-position denotes a 1-methyl-benzimidazol-2-yl, 1-(2-morpholinoethyl)-imidazol-4-yl, 5,6,7,8-tetrahydro-imidazo[1,2-a]pyridin-2-yl or butanesultam-1-yl group, $R_3$ denotes an ethyl or n-propyl group and $R_4$ denotes a sulphonyl group substituted by a hydroxy, dimethylaminocarbonylamino, phenylcarbonylamino, cycloalkylaminocarbonylamino or benzylaminocarbonylamino group, wherein the cycloalkyl moiety may contain 5 or 6 carbon atoms and the phenyl moiety may be substituted by a methoxy group, or $R_4$ denotes trifluoroacetylamino, trifluoromethylsulphonylamino, 1,3-thiazolidin-2,4-dione- 5-methylidene or 1,2,4-oxadiazol-5-on-3-yl group, and the salts thereof.

The following are examples of preferred compounds:
(a) 4'-[(2-n-propyl-4-methyl-6-(1-methylbenzimidazol-2-yl)-benzimidazol-1-yl)-methyl]-2-(1,3-thiazolidin-2,4-dione-5-methylidinyl)-biphenyl,
(b) 4'-[(2-n-propyl-4-methyl-6-(1-methylbenzimidazol-2-yl)-benzimidazol-1-yl)-methyl]-2-sulpho-biphenyl,
(c) 4'-[(2-ethyl-4-methyl-6-(5,6,7,8-tetrahydro-imidazo[1,2-a]pyridin- 2-yl)-benzimidazol-1-yl)-methyl]-2-sulpho-biphenyl,
(d) 4'-[(2-n-propyl-4-methyl-6-(1-methylbenzimidazol-2-yl)-benzimidazol-1-yl)-methyl]-2-trifluoroacetylaminobiphenyl,
(e) 4'-[(2-ethyl-4-methyl-6-(5,6,7,8-tetrahydro-imidazo[1,2-a]pyridin- 2-yl)-benzimidazol- 1-yl)-methyl]-2-trifluoroacetylamino-biphenyl,
(f) 4'-[(2-n-propyl-4-methyl-6-(1-methylbenzimidazol-2-yl)-benzimidazol-1-yl)-methyl]-2-(4-methoxy-benzylamino-carbonylaminosulphonyl)-biphenyl,
(g) 4'-[(2-n-propyl-4-methyl-6-(1-methylbenzimidazol-2-yl)-benzimidazol-1-yl)-methyl]-2-(cyclohexylamino-carbonylaminosulphonyl)-biphenyl,
(h) 4'-[(2-n-propyl-4-methyl-6-(1-methylbenzimidazol-2-yl)-benzimidazol-1-yl)-methyl]-2-(benzoylamino-sulphonyl)-biphenyl,
(i) 4'-[(2-ethyl-4-methyl-6-(5,6,7,8-tetrahydro-imidazo[1,2-a]pyridin- 2-yl)-benzimidazol- 1-yl)-methyl]-2-(benzoylaminosulphonyl)-biphenyl,
(j) 4'-[(2-n-butyl-4-methyl-6-(propanesultam-1-yl)-benzimidazol-1-yl)-methyl]-2 -(benzoylaminosulphonyl)-biphenyl and
(k) 4'-[(2-ethyl-4-methyl-6-(5,6,7,8-tetrahydro-imidazo[1,2-a]pyridin- 2-yl)-benzimidazol- 1-yl)-methyl]-2-(cyclohexylaminocarbonylaminosulphonyl)-biphenyl
and the physiologically acceptable salts thereof.

According to the invention, the new compounds are obtained by the following methods:

a) reaction of a benzimidazole of general formula

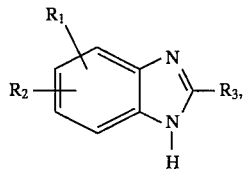

(II)

wherein
R$_1$ to R$_3$ are as hereinbefore defined, with a biphenyl compound of general formula

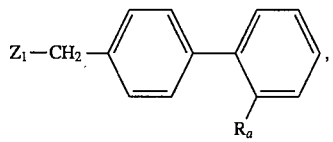

(III)

wherein
R$_a$ has the meanings hereinbefore given for R$_4$, but a reactive hydrogen atom present is protected by a conventional protecting group such as an alkoxycarbonyl group having a total of 2 to 6 carbon atoms or a benzyloxycarbonyl group and
Z$_1$ denotes a nucleophilic leaving group such as a halogen atom, e.g. a chlorine, bromine or iodine atom, or a substituted sulphonyloxy group, e.g. a methanesulphonyloxy, benzenesulphonyloxy or p-toluenesulphonyloxy group, optionally with subsequent cleaving of any protecting group used.

The reaction is conveniently carried out in a solvent or mixture of solvents such as methylene chloride, diethylether, tetrahydrofuran, dioxane, dimethyl-sulphoxide, dimethylformamide, dimethylacetamide or benzene, optionally in the presence of an acid binding agent such as sodium carbonate, potassium carbonate, sodium hydroxide, potassium tert.-butoxide, sodium hydride, triethylamine or pyridine, whilst the latter two may simultaneously also be used as solvent, preferably at temperatures between 0° and 100° C., e.g. at temperatures between ambient temperature and 50° C.

The optional subsequent cleaving of a protecting group used is preferably carried out by hydrolysis in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, ethanol/water, water/isopropanol or water/dioxane or in the presence of a primary amine such as methylamine, ethylamine or propylamine at temperatures between −10° and 120° C., e.g. at temperatures between ambient temperature and the boiling temperature of the reaction mixture.

In the reaction, a mixture of the 1- and 3-isomers is preferably obtained from which the corresponding 1-isomer can, if desired, subsequently be separated out, by crystallisation or chromatography using a substrate such as silica gel or aluminium oxide.

b) In order to prepare compounds of general formula I, wherein R$_4$ denotes a hydroxymethyl group:

Reduction of a compound of general formula

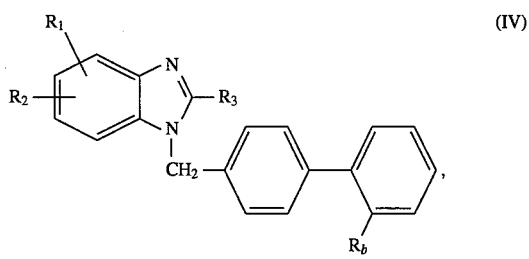

(IV)

wherein
R$_1$ to R$_3$ are as hereinbefore defined and
R$_b$ denotes an esterified carboxy group, e.g. an alkoxycarbonyl group having a total of 2 to 10 carbon atoms, a phenylalkoxycarbonyl group having 1 to 4 carbon atoms in the alkyl moiety or a phenyloxycarbonyl group.

The reduction is carried out in a suitable solvent such as methanol, methanol/water, ethanol, ether, tetrahydrofuran, dioxane or glacial acetic acid in the presence of a metal hydride such as sodium borohydride, lithium borohydride or lithium aluminium hydride at temperatures between 0° and 50° C., but preferably at temperature between 15° and 25° C.

c) In order to prepare compounds of general formula I, wherein $R_4$ denotes a formyl group:
Oxidation of a compound of general formula

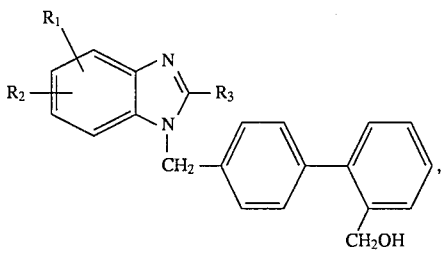
(V)

wherein
$R_1$ to $R_3$ are as hereinbefore defined.

The oxidation is preferably carried out in a solvent or mixture of solvents, e.g. in water, water/pyridine, acetone, glacial acetic acid, methylene chloride, glacial acetic acid/acetic anhydride, dilute sulphuric acid or trifluoroacetic acid, with an oxidising agent at temperatures between 0° and 80° C., preferably at temperatures between 15° and 25° C., e.g. with manganese dioxide, potassium permanganate or ruthenium dioxide at 20° C., with chromic acid in glacial acetic acid, sulphuric acid or pyridine or in acetone at 0° to 20° C. or with dimethylsulphoxide/oxalyl chloride at 0° to 20° C.

d) In order to prepare compounds of general formula I wherein $R_4$ denotes a thiazolidin-2,4-dione-5-methylidene group:
Reaction of a compound of general formula

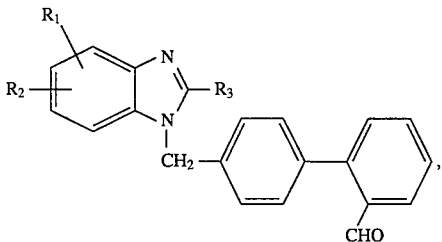
(VI)

wherein
$R_1$ to $R_3$ are as hereinbefore defined, with thiazolidin-2,4-dione.

The reaction is preferably carried out in a solvent such as glacial acetic acid, propionic acid or acetic anhydride at elevated temperatures, e.g. at temperatures between 80° and 120° C., but preferably at the boiling temperature of the solvent used.

e) In order to prepare compounds of general formula I wherein $R_4$ denotes an amino group optionally substituted by an alkoxycarbonyl group having a total of 2 to 6 carbon atoms:
Reacting a compound of general formula

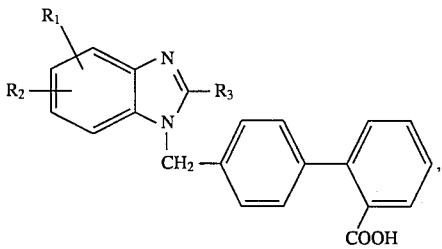
(VII)

optionally formed in the reaction mixture, wherein
$R_1$ to $R_3$ are as hereinbefore defined, with sodium azide, subsequently reacting with water or an aliphatic $C_{1-5}$-alcohol and optionally thereafter splitting off a $C_{2-6}$-alkoxycarbonyl group.

The reaction is preferably carried out in a solvent such as chloroform/water with sodium azide in the presence of a tetraalkylammonium chloride such as tetrabutylammonium chloride at temperatures of between −5° and 20° C., but preferably at 0° C.

The subsequent reaction with water or an alcohol preferably takes place in an aqueous solvent, e.g. in water, isopropanol/water, tetrahydrofuran/water or dioxane/water or in the presence of an alcohol such as methanol, ethanol, propanol, isopropanol, tert.butanol or pentanol at temperatures between 0° and 100° C., preferably at the boiling temperature of the reaction mixture.

The optional subsequent cleaving of any protecting group used is preferably carried out by hydrolysis in the presence of an acid such as hydrochloric, sulphuric, phosphoric, trichloroacetic or trifluoroacetic acid or in the presence of a base such as sodium hydroxide or potassium hydroxide in a suitable solvent such as water, water/methanol, ethanol, ethanol/water, water/isopropanol or water/dioxane or in the presence of a primary amine such as methylamine, ethylamine or propylamine at temperatures between −10° and 120° C., e.g. at temperatures between ambient temperature and the boiling temperature of the reaction mixture.

f) In order to prepare compounds of general formula I, wherein $R_4$ denotes a sulpho group:
Reaction of a compound of general formula

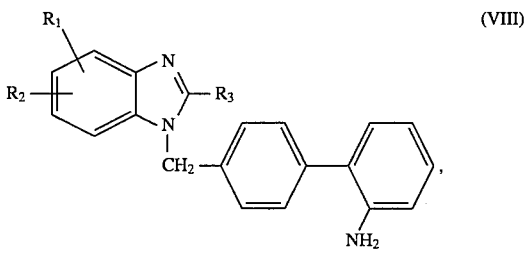
(VIII)

wherein
$R_1$ to $R_3$ are as hereinbefore defined, with a nitrite and subsequent reaction with sulphur dioxide.

The diazonium salt is conveniently prepared in a solvent, e.g. in water/hydrochloric acid, water/sulphuric acid, methanol/hydrochloric acid, ethanol/hydrochloric acid or dioxane/hydrochloric acid, by diazotising a compound of general formula VIII with a nitrite, e.g. sodium nitrite or an ester of the nitrous acids, at lower temperatures, e.g. at temperatures between −10° and 5° C. The subsequent reaction with sulphur dioxide is conveniently carried out in the presence of copper(II)chloride in a solvent such as water, methanol/water or water/hydrochloric acid at lower temperatures, e.g. at temperatures between −10° and 5° C.

g) In order to prepare compounds of general formula I wherein $R_4$ denotes an amino group substituted by an alkoxycarbonyl group having a total of 2 to 6 carbon atoms, or by a trifluoroacetyl or trifluoromethylsulphonyl group:

Reacting a compound of general formula

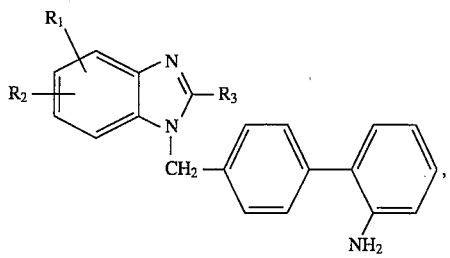

(VIII)

wherein $R_1$ to $R_3$ are as hereinbefore defined, is reacted with a compound of general formula $$Z_2-X-R_c,$$ (IX)

wherein $R_c$ denotes a $C_{1-5}$-alkoxy group or a trifluoromethyl group,

X denotes a carbonyl or sulphonyl group and $Z_2$ denotes a leaving group such as a halogen atom, e.g. a chlorine or bromine atom, an azido group or an acyloxy group, e.g. the acetoxy, methoxycarbonyloxy, ethoxycarbonyloxy or isobutoxycarbonyloxy group or, if $R_b$ denotes a trifluoromethyl group, a hydroxy group.

The reaction is conveniently carried out in a solvent such as methanol, methylene chloride, chloroform, carbon tetrachloride, ether, tetrahydrofuran, dioxane, benzene, toluene, acetonitrile, sulpholane or dimethylformamide, optionally in the presence of an organic or inorganic base, optionally in the presence of an acid-activating agent, optionally in the presence of a dehydrating agent or optionally an agent which activates the amino group, at temperatures between -20° and 200° C., but preferably at temperatures between -10° and 160° C.

If $Z_2$ denotes a hydroxy group, the acylation is conveniently carried out in a solvent such as tetrahydrofuran, ethylene chloride, chloroform, sulpholane or dimethylformamide, in the presence of an acid-activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, -potassium carbonate, potassium-tert.butoxide or 1-hydroxy-benzotriazole/triethylamine or in the presence of a tertiary organic base such as 4-dimethylaminopyridine, triethylamine, N-ethyl-diisopropylamine, N-methyl-morpholine or pyridine, which may simultaneously be used as solvent, at temperatures between -10° and 100° C., but preferably at temperatures between 0° and 50° C.

However, the acylation or sulphonylation is preferably carried out with a corresponding acid halide or acid anhydride, optionally in the presence of an acid binding agent as described hereinbefore.

h) In order to prepare compounds of general formula I, wherein $R_4$ denotes a sulphamoyl group:
Reacting a compound of general formula

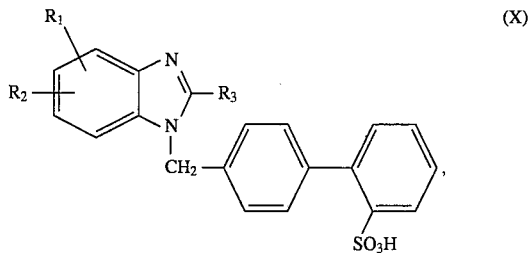

(X)

wherein $R_1$ to $R_3$ are as hereinbefore defined, or the reactive derivatives thereof, with ammonia.

The reaction is conveniently carried out in a solvent such as tetrahydrofuran, chloroform or dimethylformamide in the presence of an acid activating agent or a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, and optionally in the presence of a base such as sodium carbonate(potassium carbonate, potassium tert.butylate or 1-hydroxy-benzotriazole/triethylamine or in the presence of a tertiary organic base such as triethylamine, N-ethyl-diisopropylamine, N-methyl-morpholine or pyridine, which may simultaneously be used as solvent, at temperatures between -30° and 100° C., but preferably at temperatures between -10° and 80° C. However, the reaction may also be carried out with a corresponding acid halide or acid anhydride, optionally in the presence of an acid-binding agent as described hereinbefore.

i) In order to prepare a compound of general formula I, wherein denotes a sulphamoyl group:
Cleaving a protecting group from a compound of general formula

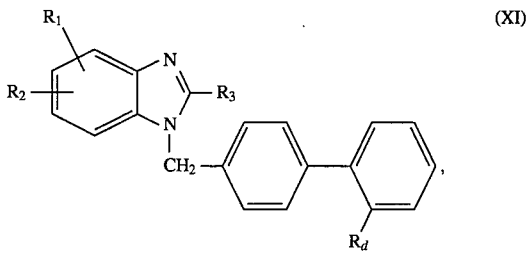

(XI)

wherein $R_1$ to $R_3$ are as hereinbefore defined and $R_c$ denotes a group which may be converted into a sulphamoyl group by hydrolysis, aminolysis or treatment with acids.

The hydrolysis is conveniently carried out either in the presence of an acid such as hydrochloric, sulphuric, phosphoric, trichloroacetic or trifluoroacetic acid, or in the presence of a base such as sodium hydroxide or potassium hydroxide in a suitable solvent such as water, water/methanol, ethanol, water/ethanol, water/isopropanol or water/dioxane and aminolysis is carried out in the presence of a primary amine such as methylamine, ethylamine or propylamine at temperatures between -10° C. and 120° C., e.g. at temperatures between ambient temperature and the boiling temperature of the reaction mixture.

j) In order to prepare compounds of general formula I wherein $R_4$ denotes a sulphonyl group substituted by an alkylcarbonylamino, alkoxycarbonylamino, alkylaminocarbonylamino, dialkylaminocarbonylamino, cycloalkylcarbonylamino, cycloalkylaminocarbonylamino, phenylcarbonylamino, phenylaminocarbonylamino, phenylalkylcarbonylamino or phenylalkylaminocarbonyl-amino group, wherein the alkyl moiety may contain 1 to 3 carbon atoms, the cycloalkyl moiety may contain 5 to 7 carbon atoms and the phenyl nucleus may be substituted by a fluorine, chlorine or bromine atom or by a methoxy group:

Reacting a compound of general formula

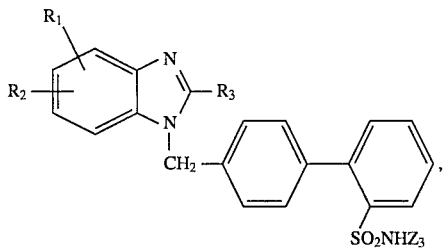
(XII)

with a compound of general formula $$Z_4-R_{d'}$$ (XIII)

wherein $R_1$ to $R_3$ are as hereinbefore defined, $Z_3$ denotes an alkoxycarbonyl group having a total of 2 to 6 carbon atoms, $Z_4$ denotes a hydrogen atom and $R_e$ denotes an alkylamino, dialkylamino, cycloalkylamino, phenylamino or phenylalkylamino group or $Z_3$ denotes a hydrogen atom, $Z_4$ denotes a $Z_5$—CO— group, wherein $Z_5$ represents a leaving such as a halogen atom, e.g. a chlorine or bromine atom, an azido group or an acyloxy group, e.g. an acetoxy, methoxycarbonyloxy, ethoxycarbonyloxy or isobutoxycarbonyloxy group, or $Z_5$ together with the hydrogen atom of an imino group adjacent to the carbonyl group represents another carbon-nitrogen bond, and $R_e$ denotes an alkyl, alkoxy, alkylamino, dialkylamino, cycloalkyl, cycloalkylamino, phenyl, phenylamino, phenylalkyl or phenylalkylamino group, whilst in the above-mentioned the alkyl moiety may contain 1 to 3 carbon atoms, the cycloalkyl moiety may contain 5 to 7 carbon atoms and the phenyl nucleus may be substituted by a fluorine, chlorine or bromine atom or by a methoxy group.

The reaction is conveniently carried out in a solvent such as methanol, methylene chloride, chloroform, carbon tetrachloride, ether, tetrahydrofuran, dioxane, benzene, toluene, acetonitrile, sulpholane or dimethylformamide, optionally in the presence of an inorganic or organic base, optionally in the presence of an acid-activating agent, optionally in the presence of a dehydrating agent or optionally an agent which activates the amino group, at temperatures between −20° and 200° C., but preferably at temperatures between −10° and 160° C.

k) In order to prepare compounds of general formula I, wherein $R_4$ denotes a 2,5-dihydro-5-oxo-1,2,4-oxadiazol-3-yl group:

Reacting a compound of general formula

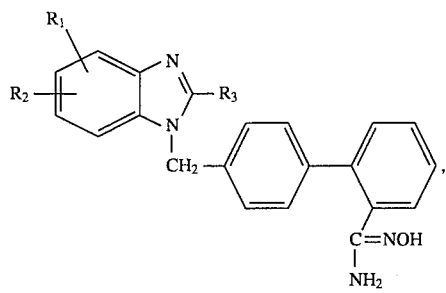
(XIV)

optionally formed in the reaction mixture, wherein $R_1$ to $R_3$ are as hereinbefore defined, with a compound of general formula $$Z_6-CO-OR_f$$ (XV)

wherein $Z_6$ represents a nucleophilic leaving group such as an halogen atom, e.g. a chlorine, bromine or iodine atom, and $R_f$ denotes an alkyl, aryl or aralkyl group, preferably a lower alkyl group such as a methyl, ethyl, n-propyl or isopropyl group, with subsequent cyclisation of an acylated amidoxime thus obtained.

The reaction is conveniently carried out in a solvent such as methylene chloride, chloroform, tetrahydrofuran, dioxane or acetonitrile, preferably in the presence of an inorganic base such as sodium or potassium carbonate or an organic base such as triethylamine or pyridine, whilst a tertiary organic base can be used as solvent at the same time, at temperatures between 0° and 20° C.

The subsequent cyclisation of an acylated amidoxime thus obtained is conveniently carried out in an organic solvent such as benzene, toluene, xylene, tetrahydrofuran or dioxane at elevated temperatures, e.g. at temperatures between 50° and 100° C., preferably at the boiling temperature of the solvent used.

The amidoxime required for this is expediently obtained by reacting a corresponding nitrile with hydroxylamine in the present of a solvent such as methanol, ethanol, methylene chloride, chloroform, dimethylformamide, tetrahydrofuran or dioxane in the presence of a suitable base such as sodium carbonate, potassium carbonate, sodium hydroxide, triethylamine, sodium methoxide, sodium ethoxide or sodium hydride at temperatures between 50° and 100° C.

In the reactions described hereinbefore, any reactive groups present such as hydroxy, amino or alkylamino groups may be protected during the reaction by means of conventional protecting groups which are split off again after the reaction.

By way of example, protecting groups for a hydroxy group may include the trimethylsilyl, acetyl, benzoyl, methyl, ethyl, tert.butyl, benzyl or tetrahydropyranyl group and protecting groups for an amino, alkylamino or imino group may include the acetyl, benzoyl, ethoxycarbonyl or benzyl group.

The optional subsequent cleaving of a protecting group is preferably carried out by hydrolysis in an aqueous solvent, e.g. in water, isopropanol/water, tetrahydrofuran/water or dioxane/water, in the presence of an acid such hydrochloric acid or sulphuric acid or in the presence of an alkali metal base such as sodium hydroxide or potassium hydroxide, at temperatures between 0° and 100° C., preferably at the boiling temperature of the reaction mixture. However, a benzyl group is preferably cleaved by hydrogenolysis, e.g. with hydrogen in the presence of a catalyst such as palladium/charcoal, in a solvent such as methanol, ethanol, ethyl acetate or glacial acetic acid, optionally with the addition of an acid such as hydrochloric acid, at temperatures between 0° and 50° C., but preferably at ambient temperature, and under a hydrogen pressure of from 1 to 7 bar, but preferably from 3 to 5 bar.

An isomer mixture of a compound of general formula I thus obtained may if desired be resolved by chromatography using a substrate such as silica gel or aluminium oxide.

Moreover, the compounds of general formula I obtained may be converted into the acid addition salts thereof, more particularly for pharmaceutical use into the physiologically acceptable salts thereof with inorganic or organic acids. Suitable acids for this purpose include hydrochloric acid, hydrobromic acid, sulphuric acid, phosphoric acid, fumaric acid, succinic acid, lactic acid, citric acid, tartaric acid or maleic acid.

Furthermore, the new compounds of general formula I thus obtained may if desired subsequently be convened into the addition salts thereof with inorganic or organic bases, more particularly for pharmaceutical use into the physiologically acceptable salts thereof. Suitable bases include for example sodium hydroxide, potassium hydroxide, lysine, methylglucamine, cyclohexylamine, ethanolamine, diethanolamine and triethanolamine.

The compounds of general formulae II to XV used as starting materials are known from the literature in some cases (see EP-A-0,502,314) or may be obtained by methods known from the literature.

Thus, for example, a compound of general formula II is obtained by acylation of a corresponding o-phenylenediamine and subsequent cyclisation or by acylation of a corresponding o-amino-nitro compound, followed by reduction of the nitro group and cyclisation, whilst any NH-benzimidazole thus obtained may be converted by alkylation with a corresponding biphenyl derivative into a compound which is correspondingly substituted in the 1-position, optionally with subsequent removal of any protecting group used.

The new compounds of general formula I and the physiologically acceptable salts thereof have valuable pharmacological properties. They are angiotensin-antagonists, particularly angiotensin-II-antagonists.

For example, the following compounds

A=4'-[(2-n-propyl-4-methyl-6-(1-methylbenzimidazol-2-yl)-benzimidazol-1-yl)methyl]-2-(1,3-thiazolidin-2,4-dione-5-methylidinyl)-biphenyl, B=4'-[(2-n-propyl-4-methyl-6-(1-methylbenzimidazol-2-yl)-benzimidazol-1-yl)methyl]-2-sulpho-biphenyl, C=4'-[(2-ethyl-4-methyl-6-(5,6,7,8-tetrahydro-imidazo[1,2-a]pyridin-2 -yl)-benzimidazol-1-yl)-methyl]-2-sulpho-biphenyl, D=4'-[(2-n-propyl-4-methyl-6-(1-methylbenzimidazol-2-yl)-benzimidazol-1 -yl)methyl]-2-trifluoroacetylamino-biphenyl, E=4'-[(2-ethyl-4-methyl-6-(5,6,7,8-tetrahydro-imidazo[1,2-a]pyridin-2 -yl)-benzimidazol-1-yl)-methyl]-2-trifluoroacetylamino-biphenyl, F=4'-[(2-n-propyl-4-methyl-6-(1-methylbenzimidazol-2-yl)-benzimidazol-1-yl)methyl]-2-(4-methoxy-benzylamino-carbonylaminosulphonyl)-biphenyl, G=4'-[(2-n-propyl-4-methyl-6-(1-methylbenzimidazol-2-yl)-benzimidazol-1-yl)methyl]-2-(cyclohexylaminocarbonylaminosulphonyl)-biphenyl, H=4'-[(2-n-propyl-4-methyl-6-(1-methylbenzimidazol-2-yl)-benzimidazol-1-yl)methyl]-2-(benzoylamino-sulphonyl)-biphenyl, I=4'-[(2-ethyl-4-methyl-6-(5,6,7,8-tetrahydro-imidazo[1,2-a]pyridin-2 -yl)-benzimidazol-1-yl)-methyl]-2-(benzoylaminosulphonyl)-biphenyl, J=4'-[(2-n-butyl-4-methyl-6-(propanesultam-1-yl)-benzimidazol-1-yl)-methyl]-2 -(benzoylaminosulphonyl)-biphenyl and K=4'-[(2-ethyl-4-methyl-6-(5,6,7,8-tetrahydro-imidazo [1,2-a]pyridin-2 -yl)-benzimidazol-1-yl)-methyl]-2-(cyclohexylaminocarbonylaminosulphonyl)-biphenyl were investigated for their biological activies as follows:

Angiotensin-II-receptor binding

The tissue (rat's lung) is homogenised in tris buffer (50 mMol Tris, 150 mMol NaCl, 5 mMol EDTA, pH 7.40) and centrifuged twice for 20 minutes each time at 20,000×g. The resulting pellet is resuspended in incubation buffer (50 mMol Tris, 5 mMol $MgCl_2$, 0.2% BSA, pH 7.40) 1:75, based on the moist weight of the tissue. Each 0.1 ml of homogenate is incubated for 60 minutes at 37° C. with 50 pM [$^{125}$I]-angiotensin-II (NEN, Dreieich, FRG) and increasing concentrations of the test substance in a total volume of 0.25 ml. The incubation is terminated by rapid filtration through glass fibre filter mats. The filters are each washed with 4 ml of ice cold buffer (25 mMol Tris, 2.5 mMol $MgCl_2$, 0.1% BSA, pH 7.40). The bound radioactivity is measured in a gamma-counter. The corresponding $IC_{50}$ value is determined from the dosage-activity curve.

Substances A to H show the following $IC_{50}$ values in the test described:

| Substance | $IC_{50}$ [nM] |
| --- | --- |
| A | 94.0 |
| B | 8.0 |
| C | 3.4 |
| D | 40.0 |
| E | 28.0 |
| F | 110.0 |
| G | 310.0 |
| H | 78.0 |
| I | 36.0 |
| J | 13.9 |
| K | 73.0 |

Moreover, when the above compounds were administered in doses of up to 30 mg/kg by intravenous route no toxic side effects were observed such as negative inotropic effects, nor any disturbances in heart rhythm. The compounds are therefore well tolerated.

The new compounds and the physiologically acceptable addition salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarct and for treating diabetic nephropathy, glaucoma, gastrointestinal diseases and bladder diseases.

Furthermore, the new compounds and the physiologically acceptable salts thereof are suitable for treating pulmonary diseases, e.g. lung oedema and chronic bronchitis, for preventing arterial re-stenosis after angioplasty, for preventing thickening of the vascular walls after vascular operations, arteriosclerosis and diabetic angiopathy. Because of the effect of angiotensin on the release of acetylcholine and dopamine in the brain, the new angiotensin antagonists are also suitable for alleviating central nervous system disorders, e.g. depression, Alzheimer's disease, Parkinson's syndrome and bulimia, as well as disorders of cognitive functions.

The dosage required to achieve these effects in adults is appropriately, when administered intravenously, 0.5 to 100 mg, preferably 1 to 70 mg, and, when administered orally, 0.1 to 200 mg, preferably 1 to 100 mg, 1 to 3 times a day. For this purpose, the compounds of general formula I prepared according to the invention, optionally in conjunction with other active substances such as, for example, hypotensive agents, ACE inhibitors, diuretics and/or calcium antagonists, may be incorporated together with one or more inert conventional carriers and/or diluents, e.g. with corn starch, lactose, glucose, micro-crystalline cellulose, magnesium stearate, polyvinyl-pyrrolidone, citric acid, tartaric acid, water, water/ethanol, water/glycerol, water/sorbitol, water/polyethyleneglycol, propylene-glycol, cetylstearyl alcohol, carboxymethylcellulose or fatty substances such as hard fat or suitable mixtures thereof, in conventional galenic preparations such as plain or coated tablets, capsules, powders, suspensions or suppositories.

Examples of additional active substances which may be used in the combinations mentioned above include bendroflumethiazide, chlorothiazide, hydrochlorothiazide, spironolactone, benzothiazide, cyclothiazide, ethacrinic acid, furosemide, metoprolol, prazosin, atenolol, propranolol, (di)hydralazine-hydrochloride, diltiazem, felodipine, nicardipine, nifedipine, nisoldipine, nitrendipine, captopril, enalapril, lisinopril, cilazapril, quinapril, fosinopril and ramipril. The dosage of these active substances is conveniently 1/5 of the lowest dose normally recommended up to 1/1 or the normally recommended dosage, that is for example 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipine or 5 to 60 mg of nitrendipine.

The following Examples are intended to illustrate the invention:

EXAMPLE 1

4'-[(2-n-Propyl-4-methyl-6-(1-methylbenzimidazol-2-yl)-benzimidazol-1-yl)-methyl]-2-hydroxymethyl-biphenyl 5.4 g of 4'-[(2-n-propyl-4-methyl-6-(1-methylbenzimidazol-2-yl)benzimidazol-1 -yl)methyl]-2-tert.butoxycarbonyl-biphenyl in 100 ml of tetrahydrofuran are added at ambient temperature to 0.7 g of lithium aluminium hydride in 100 ml of tetrahydrofuran and stirred for 2 hours at ambient temperature. The mixture is then poured onto ice water, extracted with ethyl acetate and concentrated by evaporation. After column chromatography on silica gel using dichloromethane/ethanol (97:3) the desired product is obtained which is taken for further processing in its crude state.

Yield: 2.9 g.

$R_f$ value: 0.5 g (silica gel; ethyl acetate/ethanol/ammonia= 90:10:1)

EXAMPLE 2

4-[(2-n-Propyl-4-methyl-6-(1-methylbenzimidazol-2-yl)-benzimidazol-1-yl)-methyl]-2-formyl-biphenyl 2 g of 4'-[(2-n-Propyl-4-methyl-6-(1-methylbenzimidazol-2-yl)-benzimidazol-1 -yl)-methyl]-2-hydroxymethyl-biphenyl are mixed with 2.5 g of manganese dioxide in 25 ml of dichloromethane and the mixture is stirred for 12 hours at ambient temperature. It is then filtered over kieselguhr and washed with dichloromethane. After evaporation 1.84 g are obtained as a light yellow foam.

$R_f$ value: 0.6 (silica gel; ethyl acetate/ethanol/ammonia= 90:10:1)

EXAMPLE 3

4'-[(2-n-Propyl-4-methyl-6-(1-methylbenzimidazol-2-yl)benzimidazol-1-yl)-methyl]-2-(1,3-thiazolidin-2,4-dione-5-methylidinyl)-biphenyl 1.8 g of 4-[(2-n-Propyl-4-methyl-6-(1-methyl-benzimidazol-2-yl)-benzimidazol-1 -yl)-methyl]-2-formyl-biphenyl, dissolved in 15 ml of glacial acetic acid, are heated to 120° C. with 0.62 g of thiazolidin-2,4-dione and stirred for 12 hours at this temperature. After evaporation, the mixture is chromatographed on silica gel with dichloromethane/ethanol (17:1). Then 1.4 g of the eluted product are dissolved in 50 ml of ethanol and 10 ml of 2N sodium hydroxide solution are added. After stirring for 1 hour at ambient temperature, 40 ml of water are added and the alcohol is evaporated off in vacuo. The product is extracted with ethyl acetate, dried over sodium sulphate and concentrated by evaporation.

Yield: 1.1 g,

Melting point: 252°–254° C.

EXAMPLE 4

4'-[(2-n-Propyl-4-methyl-6-(1-methylbenzimidazol-2-yl)-benzimidazol-1-yl)-methyl]-2-tert.butoxycarbonyl-amino-biphenyl 12.4 g of 4'-[(2-n-Propyl-4-methyl-6-(1-methylbenzimidazol-2-yl)-benzimidazol-1 -yl)-methyl]-2-carboxy-biphenyl, dissolved in 150 ml of chloroform, are mixed with 3.5 ml of triethylamine and then at 0° C. 3 ml of ethylchloroformate are added. After stirring for 1 hour at 0° C., 0.2 g of tetrabutylammonium bromide followed by 2.4 g of sodium azide in 8.5 ml of water are added dropwise. After 1 hour, 50 ml of chloroform and water are added, the chloroform-phase is dried over sodium sulphate and concentrated by evaporation. The product is taken up in tert.butanol and refluxed for 3 hours. After evaporation, 4.8 g of crude product are obtained which is chromatographed on silica gel with dichloromethane/ethanol (19:1).

Yield: 3.1 g,

Melting point: 182°–184° C.

EXAMPLE 5

4'-[(2-n-Propyl-4-methyl-6-(1-methylbenzimidazol-2-yl)-benzimidazol-1-yl)-methyl]-2-amino-biphenyl 10.3 g of 4'-[(2-n-Propyl-4-methyl-6-(1-methylbenzimidazol-2-yl)-benzimidazol-1 -yl)-methyl]-2-tert.butoxycarbonylamino-biphenyl are refluxed for 1 hour with 10 ml of trifluoroacetic acid in 50 ml of dichloromethane. After cooling, the mixture is neutralised with saturated sodium bicarbonate solution, the dichloromethane phase is dried over sodium sulphate and concentrated by evaporation.

Yield: 8.2 g,

Melting point: 208°–210° C. (acetone).

EXAMPLE 6

4'-[(2-n-Propyl-4-methyl-6-(1-methylbenzimidazol-2-yl)-benzimidazol-1-yl)-methyl]-2-sulpho-biphenyl 9.0 g of 4'-[(2-n-Propyl-4-methyl-6-(1-methyl-benzimidazol-2-yl)-benzimidazol-1 -yl)-methyl]-2-amino-biphenyl are suspended in 170 ml of 6N hydrochloric acid and at 0°–5° C. within 1 hour 1.95 g of sodium nitrite in 30 ml of water are added dropwise. Then the mixture is stirred for a further 2 hours at 0° C. and mixed with urea. The resulting solution is added dropwise at 0°–5° C. to a mixture consisting of 40 ml of a saturated solution of sulphur dioxide in glacial acetic acid and 2.25 g of copper(II)chloride-monohydrate in 3.3 ml of water. Then the mixture is stirred for a further 2 hours at ambient temperature, made alkaline with concentrated ammonia with cooling and the product precipitated is suction filtered. The filtrate is extracted with ethyl acetate and the ethyl acetate phase is concentrated by evaporation with the precipitate. After chromatography on silica gel with dichloromethane/ethanol (19:1), 4.2 g are obtained, melting point 307°–310° C.

EXAMPLE 7

4'-[(2-Ethyl-4-methyl-6-(5,6,7,8-tetrahydro-imidazo-[1,2-a]pyridin-2-yl)-benzimidazol-1-yl)-methyl]-2-sulpho-biphenyl Prepared analogously to Examples 4 to 6 from 4'-[(2-ethyl-4-methyl-6-(5,6,7,8 -tetrahydro-imidazo[1,2-a]-pyridin-2-yl)-benzimidazol-1-yl)-methyl]-2-carboxybiphenyl.

Melting point: >330° C.

EXAMPLE 8

4'-[(2-n-Propyl-4-methyl-6-(1-methylbenzimidazol-2-yl)-benzimidazol-1-yl)-methyl]-2-trifluoroacetylamino-biphenyl 0.5 g of trifluoroacetic acid anhydride are added dropwise at −50° C. to 0.5 g of 4'-[(2 -n-propyl-4-methyl-6-(1-methylbenzimidazol-2-yl)-benzimidazol-1-yl)-methyl]-2-amino-biphenyl in 25 ml of dichloromethane and 0.5 ml of triethylamine. The mixture is then heated to ambient temperature and stirred for 4 hours at this temperature. It is then washed with water, dried over sodium sulphate and concentrated by evaporation. After chromatography on silica gel with dichloromethane/ethanol (50:1), 0.4 g are obtained, melting point 115°–120° C.

EXAMPLE 9

4'-[(2-Ethyl-4-methyl-6-(5,6,7,8-tetrahydro-imidazo-[1,2-a]pyridin-2-yl)-benzimidazol-1-yl)-methyl]-2-trifluoroacetylamino-biphenyl Prepared analogously to Example 8 from 4'-[(2-ethyl-4-methyl-6-(5,6,7,8-tetrahydroimidazo[1,2-a]-pyridin-2-yl)-benzimidazol-1-yl)-methyl]-2-amino-biphenyl.

Melting point: 246°–248° C.

EXAMPLE 10

4'-[(2-n-Propyl-4-methyl-6-(1-methylbenzimidazol-2-yl)-benzimidazol-1-yl)-methyl]-2-sulphamoyl-biphenyl 1.2 g of 4'-[(2-n-Propyl-4-methyl-6-(1-methyl-benzimidazol-2-yl)-benzimidazol-1 -yl)-methyl]-2-sulpho-biphenyl are stirred with 10 ml of pyridine at 60° C. for 1 hour. The solution is then evaporated down, the residue is stirred with acetone and suction filtered. It is then taken up in 15 ml of thionylchloride and stirred for 1 hour at 60° C. After evaporation the residue is taken up in 10 ml of dimethylformamide and stirred into 10 ml of dimethylformamide saturated with ammonia. After 15 minutes stirring at ambient temperature the mixture is evaporated down and chromatographed on silica gel with dichloromethane/ethanol (98:2).

Yield: 0.4 g,

Melting point: 143°–145° C.

EXAMPLE 11

4'-[(2-n-Propyl-4-methyl-6-(1-methylbenzimidazol-2-yl)-benzimidazol-1-yl)-methyl]-2-ethoxycarbonyl-amino-sulphonyl-biphenyl 0.3 g of 4'-[(2-n-Propyl-4-methyl-6-(1-methyl-benzimidazol-2-yl)-benzimidazol-1 -yl)-methyl]-2-sulphamoyl-biphenyl, 170 mg of potassium carbonate, 5 ml of ethyleneglycol dimethylether and 0.11 ml of ethyl chloroformate are refluxed for 1 hour. The mixture is then combined with 30 ml of ethyl acetate and 15 ml of 10% potassium dihydrogen phosphate solution, the ethyl acetate phase is dried over sodium sulphate and evaporated down. The product obtained is taken for further processing in its crude form.

$R_f$ value: 0.53 (silica gel; methylene chloride/ethanol= 19:1)

EXAMPLE 12

4'-[(2-n-Propyl-4-methyl-6-(1-methylbenzimidazol-2-yl)-benzimidazol-1-yl)-methyl]-2-(4-methoxy-benzyl-aminocarbonylamino-sulphyl)-biphenyl 0.37 g of 4'-[(2-n-Propyl-4-methyl-6-(1-methyl-benzimidazol-2-yl)-benzimidazol-1 -yl)-methyl]-2-ethoxycarbony-laminosulphonyl-biphenyl is heated to 90° C. in 5 ml of toluene with 0.1 ml of 4-methoxybenzylamine for 18 hours. The mixture is then evaporated down and chromatographed on silica gel with dichloro-methane/ethanol Yield: 0.15 g, Melting point: 150°–154° C.

EXAMPLE 13

4'-[(2-n-Propyl-4-methyl-6-(1-methylbenzimidazol-2-yl)-benzimidazol-1-yl)-methyl]-2-(cyclohexylamino-carbonylaminosulphonyl)-biphenyl 0.275 g of 4'-[(2-n-Propyl-4-methyl-6-(1-methylbenzimidazol-2-yl)-benzimidazol-1 -yl)-methyl]-2-sulphamoyl-biphenyl is refluxed for 20 hours in 2 ml of pyridine with 0.5 ml of cyclohexylisocyanate. The mixture is then evaporated down, the residue is suspended in acetone and the insoluble solid is filtered off. After the filtrate has been evaporated down the crude produce thus obtained is purified by column chromatography over silica gel (eluant: dichloromethane/ethanol=50:1).

Yield: 0.14 g,

Melting point: 174°–176° C.

EXAMPLE 14

4'-[(2-n-Propyl-4-methyl-6-(1-methylbenzimidazol-2-yl)-benzimidazol-1-yl)-methyl]-2-(N,N-dimethylaminocarbonylaminosulphonyl)-biphenyl 1.82 g of 2-n-Propyl-4-methyl-6-(1-methylbenzimidazol-2-yl)-benzimidazole, dissolved in 100 ml of dimethylsulphoxide, are combined with 0.74 g of potassium-tert.butoxide and stirred for 0.5 hours at ambient temperature. Then 3.05 g of 4'-bromomethyl-2-(N,N-dimethylaminocarbonylsulphonamide)-biphenyl (prepared analogously to EP-A-0,503,162) are added and the mixture is stirred for 16 hours at 50° C. After a further 1.5 g of the bromomethyl compound has been added the mixture is stirred for a further 8 hours at 50° C. Then ethyl acetate and 10% sodium chloride solution are added, the mixture is extracted three times with ethyl acetate, the organic phase is washed with sodium chloride solution and dried over sodium sulphate. After evaporation, the mixture is chromatographed over silica gel with dichloromethane/ethanol (9:1).

Yield: 1.9 g, $R_f$ value: 0.55 (silica gel; methylene chloride/ethanol= 50:1)

EXAMPLE 15

4'-[(2-n-Propyl-4-methyl-6-(1-methylbenzimidazol-2-yl)-benzimidazol-1-yl)-methyl]-2-sulphamoyl-biphenyl 1.9 g of 4'-[(2-n-Propyl-4-methyl-6-(1-methyl-benzimidazol-2-yl)-benzimidazol-1-yl)-methyl]-2-(N,N-dimethylaminocarbonylamino-sulphonyl)-biphenyl are stirred for 2 hours at ambient temperature with 25 ml of 40% methylamine solution in 50 ml of ethanol and then the mixture is evaporated down. The product obtained is taken for further processing in its crude form.

Yield: 1.1 g, $R_f$ value: 0.47 (silica gel; methylene chloride/ethanol= 50:1)

EXAMPLE 16

4'-[(2-n-Propyl-4-methyl-6-(1-methylbenzimidazol-2-yl)-benzimidazol-1-yl)-methyl]-2-(benzoylaminosulphonyl)-biphenyl 145 mg of benzoic acid and 192 mg of carbonyldiimidazole are stirred in 1 ml of tetrahydrofuran for 2 hours at 50° C. To this is added a solution of 163 mg of 4'-[(2-n-propyl-4-methyl-6-(1-methylbenzimidazol-2-yl)-benzimidazol-1-yl)-methyl]-2-sulphamoyl-biphenyl, 0.133 ml of 1,8-diazabicyclo-[5.4.0]undec-7-ene and 1 ml of tetrahydrofuran and the mixture is maintained at 55° C. for 2.5 hours. Then 50 ml of ethyl acetate and 20 ml of 5% citric acid are added. The organic phase is dried with sodium sulphate and evaporated down. The residue obtained is chromatographed over silica gel with dichloromethane/ethanol (95:5).

Yield: 157 mg (amorphous),

Mass spectrum: $M^+=653$

The following compounds are prepared according to Examples 14 to 16:

(1) 4'-[(2-ethyl-4-methyl-6-(5,6,7,8-tetrahydro-imidazo [1,2-a]pyridin-2 -yl)-benzimidazol-1-yl)-methyl]-2-(benzoylaminosulphonyl)-biphenyl Prepared from 2-ethyl-4-methyl-6-(5,6,7,8-tetrahydro-imidazo-[1,2-a]pyridin-2-yl)-benzimidazole Mass spectrum: $M^+=629$ (2) 4'-[(2-n-butyl-4-methyl-6-(propanesultam-1-yl)-benzimidazol-1 -yl)-methyl]-2-(benzoylaminosulphonyl)-biphenyl Prepared from 2-n-butyl-4-methyl-6-(propanesultam-1-yl)-benzimidazole Mass spectrum: $(M+H)^+=657$ (3) 4'-[[2-n-propyl-4-methyl-6-[1-(2-morpholinoethyl)-imidazol-4-yl]-benzimidazol-1-yl]-methyl]-2-(benzoylaminosulphonyl)-biphenyl Prepared from 2-n-propyl-4-methyl-6-[1-(2-morpholinoethyl)-imidazol-4-yl]-benzimidazole Mass spectrum: $M^+=702$

EXAMPLE 17

4'-[(2-Ethyl-4-methyl-6-(5,6,7,8-tetrahydro-imidazo-[1,2-a]pyridin-2-yl)-benzimidazol-1-yl)-methyl]-2-(cyclohexylaminocarbonylaminosulphonyl)-biphenyl 0.25 g of 4'-[(2-Ethyl-4-methyl-6-(5,6,7,8-tetrahydro-imidazo[1,2-a]pyridin-2 -yl-benzimidazol-1-yl)-methyl]-2-sulphamoyl-biphenyl in 2 ml of pyridine are refluxed for 6 hours with 0.5 ml of cyclohexylisocyanate. After evaporation the mixture is chromatographed on silica gel with chloromethane/ethanol (95:5).

Yield: 85 mg,

Mass spectrum: $M^+=651$

EXAMPLE 18

4'-[[2-n-Propyl-4-methyl-6-(1-methylbenzimidazol-2-yl)-1H-benzimidazol-1-yl]-methyl]-2-(hydroxycarbamidoyl)-biphenyl To a solution of 6.90 g of hydroxylamine-hydrochloride in 50 ml of dimethylsulphoxide are added 1.35 g of sodium methoxide and 3.5 g of 4'-[[2 -n-propyl-4-methyl-6-(1-methyl-benzimidazol-2-yl)-1H-benzimidazol-1-yl]-methyl]-2 -cyano-biphenyl. The reaction mixture is stirred for 20 hours at 90° C. and after cooling it is hydrolysed with ice water. The precipitate formed is suction filtered, washed with water and dried. The crude product obtained is chromatographed on silica gel, using initially ethyl acetate and then ethyl acetate/ethanol/ammonia (19:1:0.) as eluant. The uniform fractions are combined, evaporated down, triturated with ether and dried.

Yield: 0.99 g (27% of theory),

Melting point: 185°–187° C.

EXAMPLE 19

4'-[[2-n-Propyl-4-methyl-6-(1-methylbenzimidazol-2-yl)-1H-benzimidazol-1-yl]-methyl]-2-(2,5-dihydro-5-oxo-1,2,4-oxadiazol-3-yl)-biphenyl To a suspension of 960 mg of 4'-[[2-n-propyl-4-methyl-6 -(1-methylbenzimidazol-2-yl)-1H-benzimidazol-1-yl]-methyl]-2 -(hydroxycarbamidoyl)-biphenyl and 200 mg of triethylamine in 40 ml are added dropwise, at 0° C., 220 mg of ethylchloroformate. The reaction mixture is then refluxed for 6 hours. After cooling, the reaction mixture is combined with methylene chloride, washed with water and dried. The crude product obtained is chromatographed on silica gel, using first methylene chloride and then methylene-chloride/ethanol (50:1, 25:1 and 19:1) as eluant. The uniform fractions are combined, evaporated down, triturated with ether and dried.

Yield: 0.27 g (27% of theory),

Melting point: 266°–268° C.

Mass spectrum: $M^+=555$

EXAMPLE 20

4'-[[2-n-Propyl-4-methyl-6-(1-methyl-4,5,6,7-tetrahydro-benzimidazol-2-yl)-1H-benzimidazol-1-yl]-methyl]-2-(hydroxycarbamidoyl)-biphenyl Prepared analogously to Example 18 from 4'-[[2-n-propyl-4-methyl-6-(1 -methyl-4,5,6,7-tetrahydro-benzimidazol-2-yl)-1H-benzimidazol-1-yl]-methyl]-2-cyanobiphenyl and hydroxylamine/sodium methoxide.

Yield: 25% of theory,

Melting point: 221°–224° C.

EXAMPLE 21

4'-[[2-n-Propyl-4-methyl-6-(1-methyl-4,5,6,7-tetrahydro-benzimidazol-2-yl)-1H-benzimidazol-1-yl]-methyl]-2-(2,5-dihydro-5-oxo-1,2,4-oxadiazol-3-yl)-biphenyl Prepared analogously to Example 19 from 4'-[[2-n-propyl-4-methyl-6-(1 -methyl-4,5,6,7-tetrahydro-benzimidazol-2-yl)-1H-benzimidazol-1 -yl ]-methyl]-2 -(hydroxcarbamidoyl)-biphenyl and ethylchloroformate/triethylamine.

Yield: 55% of theory,

Melting point: from 199° C. (decomp.)

Mass spectrum: $M^+=558$

In the Examples of pharmaceutical formulations which follow, any suitable compound of formula I may be used as the active substance:

Example I

Tablets containing 50 mg of active substance

| | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

Example II

Coated tablets containing 50 mg of active substance

| | |
|---|---|
| Active substance | 50.0 mg |
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation:

The active substance is mixed with the excipients and moistened with an aqueous gelatin solution. After screening and drying, the granules are mixed with magnesium stearate and compressed to form tablet cores.

The cores thus produced are covered with a coating by known methods. A colouring may be added to the coating suspension or solution.

Example III

Coated tablets containing 100 mg of active substance

| | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

Example IV

Capsules containing 250 mg of active substance

| | |
|---|---|
| Active substance | 250.0 mg |
| Corn starch | 68.5 mg |
| Magnesium stearate | 1.5 mg |
| | 320.0 mg |

Preparation:

The active substance and corn starch are mixed together and moistened with water. The moist mass is screened and dried. The dry granules are screened and mixed with magnesium stearate. The final mixture is packed into size 1 hard gelatin capsules.

Example V

Oral suspension containing 50 mg of active substance per 5 ml

| | |
|---|---|
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation:

Distilled water is heated to 70° C. Hydroxyethyl-cellulose is dissolved therein with stirring. By the addition of sorbitol solution and glycerol the mixture is cooled to ambient temperature. At ambient temperature, sorbic acid, flavouring and active substance are added. The suspension is degassed with stirring to remove any air. One dose of 50 mg is contained in 5.0 ml.

Example VI

Suppositories containing 100 mg of active substance

| Active substance | 100.0 mg |
|---|---|
| Solid fat | 1600.0 mg |
| | 1700.0 mg |

Preparation:

The hard fat is melted. At 40° C. the ground active substance is homogeneously dispersed in the melt. It is cooled to 38° C. and poured into slightly chilled suppository moulds.

What is claimed is:

1. A benzimidazole of the formula

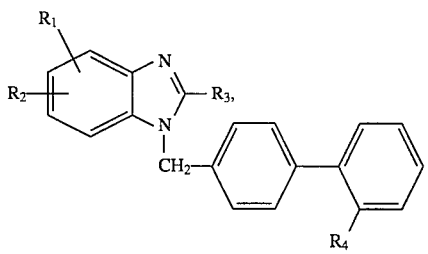

wherein $R_1$ denotes a fluorine, chlorine or bromine atom, a $C_{1-3}$-alkyl group or a trifluoromethyl group, $R_2$ denotes a 5,6,7,8-tetrahydro-imidazo[1,2-a]pyridin-2-yl group, $R_3$ denotes a $C_{1-4}$-alkyl group, a $C_{3-5}$-cycloalkyl group, an alkoxy or alkylthio group having 1 to 3 carbon atoms in the alkyl moiety and $R_4$ denotes an amino group optionally substituted by an alkoxycarbonyl group having a total of 2 to 6 carbon atoms or by a trifluoroacetyl or trifluoromethylsulphonyl group, a sulphonyl group substituted by a hydroxy, amino, alkylcarbonylamino, alkoxycarbonylamino, alkylaminocarbonylamino, dialkylaminocarbonylamino, cycloalkylcarbonylamino, cycloalkylaminocarbonylamino, phenylcarbonylamino, phenylaminocarbonylamino, phenylalkylcarbonylamino or phenylalkylaminocarbonyl-amino group, wherein the alkyl moiety may contain 1 to 3 carbon atoms, the cycloalkyl moiety may contain 5 to 7 carbon atoms and the phenyl nucleus may be substituted by a fluorine, chlorine or bromine atom or by a methoxy group, or a hydroxycarbamidoyl, thiazolidin-2,4-dione-5-methylidene or 2,5-dihydro-5 -oxo-oxadiazol-3-yl group, or a tautomer or pharmaceutically acceptable salt thereof.

2. A benzimidazole of the formula I according to claim 1, wherein $R_1$ denotes a methyl group, $R_3$ denotes a straight-chained $C_{2-4}$-alkyl group and $R_4$ denotes an amino group, a sulphonyl group substituted by a hydroxy, amino, dimethylaminocarbonylamino, phenylcarbonylamino, cycloalkylaminocarbonylamino or benzylaminocarbonylamino group, wherein the cycloalkyl moiety may contain 5 or 6 carbon atoms and the phenyl moiety may be substituted by a methoxy group, or $R_4$ may denote a trifluoroacetylamino, tert-butoxycarbonylamino, trifluoromethylsulphonylamino, 1,3-thiazolidin-2,4-dione-5-methylidene or 1,2,4 -oxadiazol-5-on-3-yl group, or a tautomer or pharmaceutically acceptable salt thereof.

3. Benzimidazoles of general formula I according to claim 1 wherein $R_1$ in the 4-position represents a methyl group, $R_2$ in the 6-position represents a 5,6,7,8-tetrahydro-imidazo[1,2-a]pyridin-2-yl group, $R_3$ denotes a straight-chained $C_{2-4}$-alkyl group and $R_4$ denotes a sulphonyl group substituted by a hydroxy, amino, dimethylaminocarbonylamino, phenylcarbonylamino, cycloalkylaminocarbonylamino or benzylaminocarbonyl-amino group, wherein the cycloalkyl moiety may contain 5 or 6 carbon atoms and the phenyl moiety may be substituted by a methoxy group, or $R_4$ denotes a trifluoroacetylamino, trifluoromethylsulphonylamino, 1,3-thiazolidin-2,4-dione-5-methylidene or 1,2,4-oxadiazol-5-on-3-yl group, or a pharmaceutically acceptable salt thereof.

4. A benzimidazole of the formula I according to claim 1, wherein $R_1$ in the 4-position denotes a methyl group, $R_2$ in the 6-position denotes a 5,6,7,8-tetrahydro-imidazo[1,2-a]pyridin-2-yl group, $R_3$ denotes an ethyl or n-propyl group and $R_4$ denotes a sulphonyl group substituted by a hydroxy, dimethylaminocarbonylamino, phenylcarbonylamino, cycloalkylaminocarbonylamino or benzylaminocarbonylamino group, wherein the cycloalkyl moiety may contain 5 or 6 carbon atoms and the phenyl moiety may be substituted by a methoxy group, or $R_4$ denotes a trifluoroacetylamino, trifluoromethylsulphonylamino, 1,3-thiazolidin-2,4 -dione-5-methylidene or 1,2,4-oxadiazol-5-on-3-yl group, or a pharmaceutically acceptable salt thereof.

5. A benzimidazole selected from the group consisting of:
(c) 4'-[(2-ethyl-4-methyl-6-(5,6,7,8-tetrahydro-imidazo[1,2-a]pyridin-2 -yl)-benzimidazol-1-yl)-methyl]-2-sulpho-biphenyl,
(e) 4'-[(2-ethyl-4-methyl-6-(5,6,7,8-tetrahydro-imidazo[1,2-a]pyridin-2 -yl)-benzimidazol-1-yl)-methyl]-2-trifluoroacetylamino-biphenyl,
(i) 4'-[(2-ethyl-4-methyl-6-(5,6,7,8-tetrahydro-imidazo[1,2-a]pyridin-2 -yl)-benzimidazol-1-yl)-methyl]-2-(benzoylaminosulphonyl)-biphenyl, and
(k) 4'-[(2-ethyl-4-methyl-6-(5,6,7,8-tetrahydro-imidazo[1,2-a]pyridin-2 -yl)-benzimidazol-1-yl)-methyl]-2-(cyclohexylaminocarbonylaminosulphonyl)-biphenyl, or a pharmaceutically acceptable salt thereof.

6. 4'-[(2-Ethyl-4-methyl-6-(5,6,7,8-tetrahydro-imidazo[1,2-a]pyridin-2 -yl)-benzimidazol-1-yl)-methyl]-2-(cyclohexylaminocarbonylaminosulphonyl)-biphenyl, or a pharmaceutically acceptable salt thereof.

7. A pharmaceutical composition, suitable for the treatment of hypertension, comprising an antihypertensive amount of a compound according to claim 1, 2, 3, 4, 5 or 6, optionally together with one or more inert carriers and/or diluents.

8. A method for the treatment of hypertension which comprises administering to a subject in need of such treatment an antihypertensive amount of a compound according to claim 1, 2, 3, 4, 5 or 6.

* * * * *